United States Patent [19]

Clemente et al.

[11] Patent Number: 5,684,038
[45] Date of Patent: Nov. 4, 1997

[54] COMPOSITION AND PROCESS FOR PREVENTION AND TREATMENT OF CUTANEOUS IMMEDIATE HYPERSENSITIVITY REACTIONS

[75] Inventors: Emmett Clemente, Manchester; Robert W. Mendes, Dedham; Aloysius O. Anaebonam, Burlington; Mumtaz Ahmed, Westford, all of Mass.

[73] Assignee: Ascent Pharmaceuticals, Inc., Billerica, Mass.

[21] Appl. No.: 672,752

[22] Filed: Jun. 28, 1996

Related U.S. Application Data

[62] Division of Ser. No. 415,722, Apr. 3, 1995, Pat. No. 5,532,270.

[51] Int. Cl.$^6$ ........................................ A01N 43/16
[52] U.S. Cl. .................. 514/456; 514/829; 514/830; 514/937
[58] Field of Search ................. 424/401; 514/456, 514/829, 830, 937

[56] References Cited

U.S. PATENT DOCUMENTS 4,271,182  6/1981  Sullivan ............................ 424/283

FOREIGN PATENT DOCUMENTS

A1-0587264  3/1994  European Pat. Off. .

*Primary Examiner*—Jyothsan Venkat
*Attorney, Agent, or Firm*—Welsh & Katz, Ltd.

[57] ABSTRACT

A process and pharmaceutical composition for the prevention and treatment of cutaneous Type I hypersensitivity reactions in humans is disclosed. The pharmaceutical composition comprises of a chromone compound of the following formula, or a pharmacologically acceptable salt, ester or amide thereof:

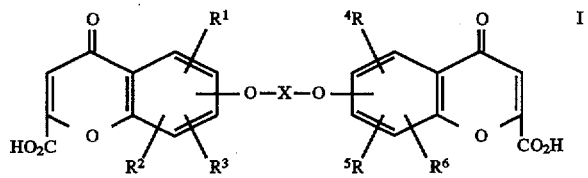

dissolved or dispersed in a pharmacologically acceptable carrier. In accordance with the process, a preventively or therapeutically effective amount of the composition is topically administered to a human patient, as required; i.e. for prevention the composition is administered to the area of skin susceptible to exposure to antigen and for treatment the composition is administered to the reaction site.

5 Claims, No Drawings

COMPOSITION AND PROCESS FOR PREVENTION AND TREATMENT OF CUTANEOUS IMMEDIATE HYPERSENSITIVITY REACTIONS

CROSS-REFERENCE TO RELATED APPLICATION

This is a division of U.S. application Ser. No. 08/415,722, filed Apr. 3, 1995, now U.S. Pat. No. 5,532,270, the benefit of filing date of which is herein claimed.

DESCRIPTION

1. Technical Field

This invention relates to the prevention and treatment of cutaneous immediate hypersensitivity reactions such as those caused by insect bites and stings, and more particularly to a composition and process for preventing and treating cutaneous immediate hypersensitivity reactions that utilizes a chromone compound of the general formula shown in formula I, hereinafter, wherein $R^1$, $R^2$, $R^3$, $R^4$, $R^5$ and $R^6$ i.e. $R^1$-$R^6$ and X are defined hereinafter.

2. Background of Invention

A compound of formula I, hereinafter, and its pharmacologically acceptable salts, esters and amides has been used successfully in the prophylactic treatment of asthma for many years. One particular compound, commonly known as cromolyn (formula II, hereinafter), is routinely used as a prophylactic treatment for asthma, rhinitis, conjunctivitis and intestinal masocytosis. These compounds do not alleviate the symptoms of asthma once an attack has begun.

Cromolyn is not a bronchial or vasodilator as is usual for asthma treatments. Rather, cromolyn acts to inhibit the release of inflammatory mediators such as histamine from several types of cells in the lungs. Inhalation of a solution containing the disodium salt of cromolyn (cromolyn sodium), on a regular schedule by an individual suffering from asthma provides a prophylactic treatment for bronchial asthma. The prophylactic response increases with the length of use of the drug.

A chromone compound corresponding to formula I and its pharmacologically acceptable salts, esters and amides has also been reported to be effective against certain atopic skin disorders such as atopic eczema and various other chronic skin conditions that involve skin mast cells and/or an antibody-antigen reaction. (Sullivan U.S. Pat. Nos. 4,362,742 and 4,271,182).

Skin conditions of the type discussed in Sullivan (atopic dermatoses) are systemic skin diseases that do not result from exposure to an externally introduced allergen, but rather are believed to have. internal causative factors. These conditions are also known or suspected to have hereditary causation or predisposition. Outbreaks of skin lesions occur periodically throughout life, often beginning in early infancy.

One common and effective treatment of the lesions associated with atopic dermatoses is topical application of corticosteroids. Oral steroids can also be given in severe cases. However care needs to be taken when using steroids for atopic dermatoses since there is often a rebound reaction when the steroid treatment is stopped.

Topical antihistamines have not been found to effective. However, the itching associated with the lesions may be relieved by large doses of oral antihistamine (for example, diphenhydramine 50 mg b.i.d or q.i.d. for adults).

Topical treatment of the lesions associated with atopic dermatosis with a compound corresponding to formula I or its pharmacologically acceptable salts, esters or amides has been shown to facilitate healing of the lesion being treated. However, treatment does not actually cure the disease itself.

Chromone compounds have also been shown to be effective against certain allergic conditions of the eye.

However, chromone compounds corresponding to formula I are not predictably or uniformly absorbed by all types of tissue and the effectiveness of these compounds against other conditions of the skin or epidermis is not predictable.

The exact mechanism of action of a chromone compound is unknown. A chromone compound is believed to possess no vasodilator, antihistaminic or anti-inflammatory activity. It is known that a chromone compound, and particularly cromolyn, is poorly absorbed by the lungs and by the gastrointestinal tract. Only about 7–8 percent of a usual total dose is absorbed from the lung, and is then rapidly excreted, unchanged, in the bile or urine. The remainder is expelled from the nose or, if swallowed, excreted by the alimentary tract.

An immediate hypersensitivity reaction, also known as a Type I hypersensitivity reaction or a Type I reaction, can occur after exposure to an allergen. Type I hypersensitivity reactions of the skin, or cutaneous Type I hypersensitivity reactions, are often the result of insect bites or stings, but can also result from exposure to other substances to which the patient is sensitive, such as latex or the saliva of an animal.

All Type I hypersensitivity reactions are characterized by a rapid response to exposure to an allergen. Physical manifestations and symptoms of the reaction typically occur between 1 and 15 minutes after exposure.

The physical manifestations and symptoms, of a cutaneous Type I reaction, can include swelling of the affected area, reddening of the skin, and mild to severe pruritus in the area directly exposed to the allergen as well as the immediate surrounding area.

Immunologically, the body upon exposure to the allergen produces IgE antibodies that bind to the surface receptors of mast cells and basophils. Upon re-exposure to the allergen, the allergen bonds to the cell-associated IgE, causing signal transduction in the mast cells and basophils and secretion of mediator. The mediator then acts upon body structures resulting in the observed physical reaction.

In Type I reactions, the pathology is related to degranulation of mast cells and the reaction caused by mediators such as histamine and leukotriene C4 (LTC4).

If left untreated, most symptoms caused by Type I hypersensitivity reactions gradually subside and then go away entirely. The time required varies considerably from individual to individual.

During the time the reaction and symptoms persist, the individual is uncomfortable, often intensely uncomfortable. If untreated, the affected area in a cutaneous Type I reaction is frequently scratched or rubbed raw. This action can result in secondary infection at the site and scarring in some instances.

There have been numerous remedies utilized for the itching caused by cutaneous Type I reactions. Topical remedies include calamine lotions, baking soda, steroids and a variety of "home" remedies. Topical as well as oral antihistamines are also often used to lessen the discomfort caused by Type I reactions. These remedies have demonstrated varying degrees of effectiveness.

Currently, prevention of a Type I reaction requires avoidance of the allergen or a participation in a desensitization program that is not always effective and generally requires years of treatment.

Although Type I reactions generally, and cutaneous Type I reactions specifically, are not usually life-threatening or dehabilitating, they do cause discomfort and at certain times of the year can occur quite often. It would therefore be advantageous to be able to prevent and effectively treat these types of reactions with a simple topically applied remedy. Disclosure of one such remedy is as follows.

BRIEF SUMMARY OF INVENTION

A process for preventing and/or treating a cutaneous Type I hypersensitivity reaction (hereinafter referred to as a Type I reaction or a cutaneous Type I reaction) is disclosed herein. The compounds utilized for prevention and for treatment are the same. The process for application of the compounds is highly similar. For both prevention and treatment, a composition containing a compound of formula I, hereinafter, is topically administered. The area to which the compound is applied and the amount of compound applied can vary for a preventative application and a therapeutic application of the composition, as explained hereinafter.

A process for prevention of a cutaneous Type I reaction utilizes topical application of a formulation containing a Type I reaction-preventing amount of a chromone compound of formula I, or a pharmacologically acceptable salt, ester or amide thereof. The particularly preferred compound is commonly referred to as cromolyn [1,3-bis(2-carboxychromon-5-yloxy)-2-hydroxypropane] and is represented in formula II, hereinafter.

It is found that a topical application of a chromone compound of formula I to area of skin susceptible to exposure to allergen capable of producing a Type I reaction, (the area to be protected) prior to exposure to allergen can prevent the onset or decrease the severity of a cutaneous Type I hypersensitivity reaction. This application can be combined with use of insect repellents to further reduce the occurrence of Type I reactions caused by insect bites or stings.

A process for treatment of a cutaneous Type I reaction utilizes topical administration of a formulation containing a symptom-reducing amount of a chromone compound of formula I, or a pharmacologically acceptable salt, ester or amide thereof to the reaction site. The particularly preferred compound is commonly referred to as cromolyn [1,3-bis(2-carboxychromon-5-yloxy)-2-hydroxypropane] and is represented in formula II, hereinafter.

It is found that topical treatment with a chromone of formula I reduces the inflammation of the reaction site and lessens or eliminates the pruritus associated with the reaction. This process of treatment results in early resolution of the Type I reaction and the accompanying symptoms, with no known side effects.

A chromone compound utilized in the present processes as the active agent for both prevention and treatment and hereinafter referred to as the "active agent" or "active ingredient", conforms to the structure of formula I, below, and includes pharmacologically acceptable salts, esters and amides thereof where $R^1$, $R^2$, $R^3$, $R^4$, $R^5$ and $R^6$; i.e. $R^1$–$R^6$ and X are further defined hereinafter.

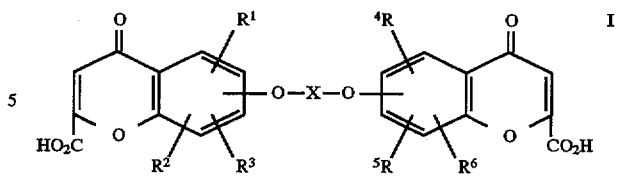

The molecule of formula I can be generally described as two chromone molecules linked by an O—X—O chain. In the above formula, and in all other formulas shown herein, hydrogen atoms that are not needed to show conformation about a particular bond are not shown.

Although $R^1$–$R^6$ can vary as fully described hereinafter, in general, it is preferred that no more than one of $R^1$, $R^2$ and $R^3$ and no more than one of $R^4$, $R^5$ and $R^6$ is other than hydrogen, and each is selected from a hydrogen, a halogen atom, a $C_1$–$C_6$ alkyl, hydroxy, $C_1$–$C_6$ ulcus or substituted ulcus group, and X is as defined hereinafter. More preferred compounds of formula I are those in which each of $R^1$–$R^6$ is hydrogen, and the carboxyl groups are present as alkali metal carboxylate salts.

The X group is preferably a straight or branched hydrocarbon chain containing 3 to 7 carbon. atoms. The chain can be interrupted by one or more oxygen atoms. Even more preferably the chain is a polyethylene chain substituted by one or more hydroxyl groups, with a 2-hydroxytrimethylene chain (—$CH_2CHOHCH_2$—) being a particularly preferred chain.

Although the above describes more preferred X groups, X can be one of a wide-variety of groups as fully set forth hereinafter.

The structure of a particularly preferred compound of formula. I is shown below as formula II, and is commonly known as cromolyn:

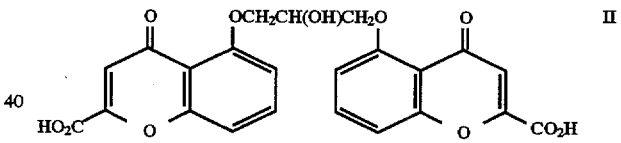

The most preferred derivative of formula II for use in the disclosed process is the disodium salt thereof, hereinafter referred to as cromolyn sodium.

A contemplated process for prevention of a cutaneous Type I reaction comprises the administration to area of skin to be protected of a composition that contains a pharmacologically acceptable carrier having dissolved or dispersed therein a preventively effective (reaction-preventing) amount of a compound of formula I or a pharmacologically acceptable salt, ester or amide thereof, as an active ingredient or agent.

That composition is topically applied to the area of the skin to be protected. The composition can be applied 4 times a day, as needed, and then either be covered or preferably left open to the air. Exemplary effective amounts, by weight, of the active ingredient can range from about 0.5 to about 5.0 percent of the total composition.

A contemplated process for treatment of cutaneous Type I reaction comprises the administration to a human with cutaneous Type I hypersensitivity reaction of a composition that contains a pharmacologically acceptable carrier having dissolved or dispersed therein a therapeutically effective (symptom-reducing) amount of a compound of formula I or a pharmacologically acceptable salt ester, or amide thereof, as an active ingredient or agent.

That composition is topically applied to the area of the skin involved in the reaction. The composition can be applied to the site several times a day and then either be covered or left open to the air. Exemplary therapeutically effective amounts, by weight, of the active ingredient can range from about 0.5 to about 10 percent of the total composition.

The composition can be used together with insect repelling agents, or can contain such agents itself if the suspected allergen is venom from insect bites or stings.

The present invention has several benefits and advantages.

One benefit is that use of the described process and composition can act to prevent the onset of a cutaneous Type I hypersensitivity reaction, without adverse side effects.

Another benefit is that use of the described process and composition can also be used to reduce or eliminate the inflammation and pruritus caused by a cutaneous Type I reaction without adverse side effects.

A further benefit is that the reduction of the physical symptoms of a cutaneous Type I reaction will reduce or eliminate scratching or rubbing of the site and thereby reduce or eliminate the possibility of secondary infections and scarring.

One advantage of the described process is that many cutaneous Type I hypersensitivity reactions can be easily prevented by the application of the composition prior to exposure to allergen.

Another advantage of the described process is that it can also be used to lessen or eliminate the symptoms of most cutaneous Type I reaction, caused by a variety of allergens.

Further benefits and advantages of the invention will be apparent to those of skill in the art from the description that follows.

DETAILED DESCRIPTION OF THE INVENTION

The present invention contemplates a process for prevention and/or treatment of cutaneous Type I hypersensitivity reaction. A contemplated process utilizes a chromone compound corresponding to formula I, preferably the compound commonly known as cromolyn, (formula II) and more preferably the disodium salt of cromolyn, (cromolyn sodium) as an active agent compound in a composition that is topically administered.

For prevention of a cutaneous Type I reaction, the composition is topically administered to the area of skin believed to be susceptible to exposure to allergens (i.e., the area to be protected). Once a cutaneous Type I reaction has occurred, a composition can be topically administered to the reaction site of humans in need of such treatment; i.e., having a cutaneous Type I hypersensitivity reaction.

A. Compounds

A chromone compound utilized in the present invention is represented by formula I.

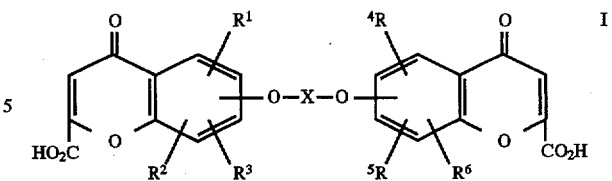

Each of $R^1$–$R^6$ can be the same, or different. Each $R^1$–$R^6$ can be a hydrogen; a halogen (halo) group or moiety (i.e. chloride, bromide, iodide or fluoride); a $C_1$–$C_6$ lower alkyl group (i.e. a methyl, ethyl, propyl, isopropyl, butyl, tertiary-butyl, or hexyl group); hydroxy; $C_1$–$C_6$ lower alkoxy (i.e. a methoxy, ethoxy, propoxy, isopropoxy, butoxy, tertiary-butoxy or hexyloxy group); substituted $C_1$–$C_6$ lower alkoxy group; or a substituted $C_1$–$C_6$ lower alkyl, as are discussed below.

The substituted lower alkyl or alkoxy group can be substituted with the following groups: hydroxyl; lower ($C_1$–$C_6$) alkoxy; carboxy or halo such as chloro- bromo- iodo- or fluoro-); $C_2$–$C_6$ lower alkenyl, e.g. allyl or methyl-allyl; benzyl; and nitro. A substituent group is not itself substituted. It is preferred that each $R^1$–$R^6$ be unsubstituted.

In general, it is preferred that no more than one of $R^1$, $R^1$, and $R^3$ and no more than one of $R^4$, $R^5$ and $R^6$ is other than hydrogen, and each is selected from a hydrogen, a halogen atom, a $C_1$–$C_6$ alkyl, hydroxy, $C_1$–$C_6$ alkoxy or substituted alkoxy group, and X is as defined before. A preferred compound is symmetric with $R^1$ being the same as $R^4$, $R^3$ being the same as $R^5$ and $R^2$ being the same as $R^6$. More preferred compounds of formula I are those in which each of $R^1$–$R^6$ is hydrogen.

The bridging X group of formula I is a saturated or unsaturated, substituted or unsubstituted, straight or branched polymethylene chain having between 3 and 10 carbon atoms can be interrupted by one or more carbocyclic rings or oxygen-containing heterocyclic rings, (e.g. benzene, dioxan, tetrahydrofuran, or dihydropyran rings), oxygen-atoms or carbonyl groups.

The X group is preferably a straight or branched hydrocarbon chain containing 3 to 7 carbon atoms. The chain can be interrupted by one or more oxygen atoms. Even more preferably, the chain is a polymethylene chain substituted by one or more hydroxyl groups, with a 2-hydroxy-trimethylene chain ($-CH_2CHOHCH_2-$) being a particularly preferred chain. The structure of a particularly preferred compound of formula I is shown below as formula II, and is commonly known as cromolyn:

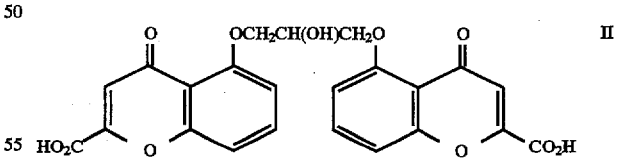

Although the above describes more preferred X groups, X can be one of a wide variety of groups as set forth hereinafter.

The X group can be a straight or branched, saturated or unsaturated hydrocarbon chain. Additionally, X can be such a chain interrupted by one or more oxygen atoms, carbonyl groups or carbocyclic or heterocyclic rings and can be substituted by one or more halogen atoms (e.g. chlorine, bromine, iodine or fluorine atoms), or hydroxy or $C_1$–$C_6$ lower alkoxy (e.g. methoxy, ethoxy, propoxy, isopropoxy, butoxy, tertiary-butoxy, etc.) groups. Some specific examples of the X group are groups of the following formulas:

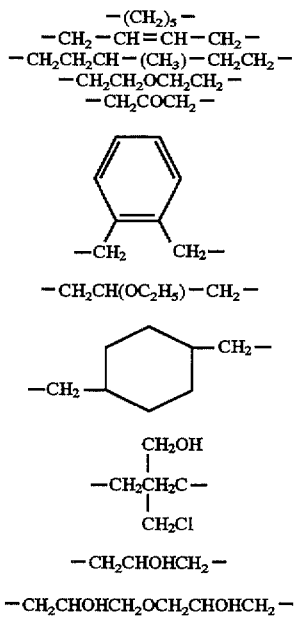

Different or corresponding positions on the chromone molecules can be linked by the O—X—O chain, although symmetrical linkages are preferred.

Pharmacologically acceptable salts of a compound of formula I or formula II suitable for use in the disclosed process include for example, ammonium salts, alkali metal salts (e.g. sodium, potassium and lithium), alkaline earth metal salts (e.g. magnesium and calcium), and salts with organic amines (e.g. mono-, di- or tri-$C_1$-$C_6$-alkyl amines, piperidine, morpholine and trialkanol $C_1$-$C_6$-alkyl amine salts).

Pharmacologically acceptable esters include simple $C_1$-$C_6$ alkyl esters (e.g. methyl, ethyl, propyl, isopropyl, butyl, tertiary-butyl and hexyl esters). Pharmacologically acceptable amides include simple amides (for example amides with ammonia and $C_1$-$C_6$ lower alkylamines such as methylamine, ethylamine, and the like whose alkyl portions are discussed before) and more complex amides with amino acids, e.g. glycine.

Specific examples of compounds of formula I and derivatives thereof are provided in U.S. Pat. No. 4,362,742, whose disclosures are incorporated herein by reference.

The most preferred derivative of formula II for use in the disclosed process is the disodium salt thereof, hereinafter referred to as cromolyn sodium.

The phrase "pharmacologically acceptable" salts, esters and amides as used herein refers to non-toxic salts, esters and amides of formula I as discussed above.

B. Compositions

A compound of formula I or one of its pharmacologically acceptable salts, esters or amides dissolved or dispersed in a preventively therapeutically effective amount in a pharmacologically acceptable carrier constitutes a composition (preparation) useful in a process of this invention. The disodium salt of a compound of formula II, where $R^1=R^2=R^3=R^4=R^5=R^6=H$, and X=—$CH_2CHOHCH_2$—, is preferred for use in treatment.

Although a compound of formula I and its pharmacologically salts, esters and amides can be administered as a pure chemical, it is preferred that it be administered as a pharmaceutical composition. In either event, a contemplated compound is administered in an amount sufficient to provide a therapeutically effective dose, for prevention or treatment, as is discussed hereinafter.

Accordingly, the present invention utilizes a pharmaceutical Composition comprising a preventively or therapeutically effective dose of a compound of formula I or a pharmacologically acceptable salt, esters or amide thereof, hereinafter referred to as the "active ingredient" or "agent", dissolved or dispersed in a pharmacologically acceptable carrier or diluent.

A preventively effective amount of a contemplated chromone compound of formula I for use in prevention of a cutaneous Type I reaction, typically constitutes about 0.5 to about 5 weight percent of a contemplated composition. More preferably, that amount is about 2 to about 4 weight percent.

A therapeutically effective amount of a contemplated chromone compound of formula I for use in treatment of a cutaneous Type I reaction typically constitutes about 0.5 to about 5 weight percent of a contemplated composition. More preferably, that amount is about 2 to about 4 weight percent.

A pharmaceutical composition is prepared by any of the process well known in the art of pharmacy all of which involve bringing into association the active ingredient and the carrier therefore. For preventative or therapeutic use, a compound utilized in the present invention can be administered in the form of conventional pharmaceutical compositions. Suchcompositions can be formulated so as to be suitable for topical administration of the active ingredient. In these compositions, the agent is typically dissolved or dispersed in a physiologically tolerable carrier or diluent.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and composition that do not produce an allergic or similar untoward reaction when administered to a human.

The pharmacologically tolerable carrier can take a wide variety of forms suitable for topical administration, such as an ointment, water-miscible ointment, cream, lotion, paste, gel or liniment. These carriers can be aqueous, oily (oleaginous) or water-miscible or water-dispersible. They can be oil-in-water or water-in-oil based emulsions. A discussion of some types of suitable carriers is present in U.S. Pat. No. 4,362,742, whose disclosures are incorporated herein by reference.

The preferred carrier composition for the disclosed process is an oil-in-water emulsion in which the active ingredient is present in the water phase. The preferred oil-in-water emulsion is comprised of a water phase containing the active ingredient. Water is typically present at about 40 to about 80 weight percent and more preferably at about 66 to about 72 weight percent of the composition.

One or more water-miscible organic solvents such as glycerine, propylene glycol can also be present in the water phase. A sequestering agent such as edetate disodium dihydrate (EDTA) can also be present, as can a pH value-adjusting acid. Phosphoric acid is also preferably used in the water phase in an amount required to obtain the required necessary pH value.

The pH value can range between about 3 and about 8. The more preferred pH value range is about 4 to about 7. The most preferred pH value is 5.5.

Compound names used herein are usually used common names as well as those utilized in the *International Cosmetic Ingredient Dictionary*, The Cosmetic, Toiletry, and Fragrance Association, Washington, D.C. (1993), and *The U.S. Pharmacopeia, The National Formulary*, [USP XXII; NF XVII] United States Pharmacopeial Convention, Inc., Rockville, Md., 1990.

The oil phase is comprised of materials that individually can be solids or liquids at room temperature, e.g. about 20° C. These materials include waxes such as white wax and emulsifying wax, squalene and a silicone oil such as dimethicone. The oil phase also contains a component of the emulsifier, a $C_2$–$C_4$ acyl polypropyleneglycol $C_{12}$–$C_{18}$ alkyl ether that contains an average of about 2–4 PPG groups per molecule. These materials impart an appropriate creamy feel to the composition upon the skin and tend to form an oleaginous layer over the treated area.

A $C_{12}$–$C_{18}$ alcohol or mixtures thereof is also preferably present. Illustrative $C_{12}$–$C_{18}$ alcohols include lauryl, myristyl, cetyl, stearyl and oleyl alcohols.

The emulsifier includes emulsifying wax and preferably a mixture of two ingredients. The first is a $C_2$–$C_4$-acyl polypropyleneglycol (PPG) $C_{12}$–$C_{18}$ alkyl ether that contains an average of about 2–4 PPG groups per molecule. The second is a polyoxyethyleneglycol (PEG) $C_{14}$–$C_{26}$ ether having an average of about 8–12 PEG groups per molecule.

The emulsifying wax and the PEG compounds are preferably present together at about 8–17 weight percent of the total preparation, and in a weight ratio of about 15:1 to about 1:1, more preferably at about 10:1 to about 8:1, and most preferably about 9:1 in the order mentioned.

The ratio of the emulsifying wax and PEG emulsifier used is designed to provide a calculated HLB number of about 8 to about 14, and more preferably about 10 to about 12. The total amount of emulsifier used is typically a function of the total amount of oil phase ingredients, with more total emulsifier being used with a greater amount of oil phase ingredients, and less total emulsifier with the lower amount of oil phase ingredients, as is well known.

Emulsifying wax has an average HLB value of about 11. A particularly preferred PPG-containing emulsifier is PPG-2 myristyl ether propionate that has an HLB value of 11. A particularly preferred PEG-containing emulsifier is polyoxyethylene-10-oleyl ether that has an HLB value of 12.4. The above HLB value ranges are calculated based upon these emulsifiers.

PPG-2 myristyl ether propionate can be replaced with one of the compounds encompassed by the designation $C_2$–$C_4$ acyl-PPG(2–4) $C_{12}$–$C_{16}$ ether. Exemplary materials include PPG-3 lauryl ether butyrate and PPG-4 stearyl ether acetate, and the like. Similarly, PEG-10-oleyl ether (oleth-10; PEG compound) can be replaced with another PEG (7–12) $C_{14}$–$C_{20}$ alkyl ether such as PEG- 12-cetyl ether (ceteth-12), PEG-7-stearyl ether (steareth-7), PEG-11-cetyl/stearyl ether (ceteareth-11), and the like.

It is noted that substitution in the PPG compound and PEG compound are considered together as these two compounds are present in the carrier in a combined total of 2–6 percent weight to weight with a weight to weight PPG-containing emulsifier to PEG-containing emulsifier ratio in the range of about 4:1–1:1, preferably about 3:1–2:1, most preferably of 2.5:1. This ratio results in the desired HLB number.

A contemplated preparation typically has a viscosity of a cream or ointment. Exemplary viscosities are thus about 20,000 to about 100,000 cps at 25° C., and more preferably about 50,000 to about 70,000 cps.

One and preferably more than one preservative is also preferably present in a commercial preparation. Exemplary preservatives include methylparaben, propylparaben and imidurea.

The following table provides a preferred range of weight to weight percentages for each particularly preferred ingredient present in a particularly preferred oil-in-water emulsion preparation for commercial use.

| Ingredient | % W/W Ranges |
| --- | --- |
| Cromolyn sodium | 0.5–10 |
| Emulsifying wax, N.F. | 8–17 total, in a ratio of 8:1 for the wax: PEG, and a 4:1-1:1 ratio for PPG:PEG |
| Polyoxy-10 Oleyl Ether, N.F. (PEG) | |
| PPG-2 Myristyl Ether Propionate | |
| Squalene, U.S.P. | 2–10 |
| White Wax, N.F. | 0.5–5 |
| Dimethicone, N.F. | 0.5–5 |
| Cetyl Alcohol, N.F. | 1–10 |
| Propylparaben, N.F. | 0.05–0.2 |
| Purified Water, U.S.P. | q.s. |
| Glycerin, U.S.P. | 1–5 |
| Edetate Disodium Dehydrate, U.S.P. | 0.01–1 |
| Propylene Glycol, U.S.P. | 1–5 |
| Methylparaben, N.F. | 0.1–0.4 |
| Imidurea, N.F. | 0.1–0.3 |
| Phosphoric Acid, N.F. | q.s. |

Changes in the specific, particularly preferred, ingredients listed are contemplated. Thus one of ordinary skill in the art can substitute similar ingredients for those discussed above without substantially altering the effectiveness of the carrier and the final composition. The viscosity of carrier can be changed so long as it remains suitable for topical application.

In addition, if a certain ingredient is changed resulting in different hydrophilic/lipophilic balance (HLB), this-can be compensated for, using known techniques, by changing another ingredient.

Specific examples of the acceptable alterations in the particularly preferred given ingredients are set forth below. Specific combinations of changes that result in acceptable compositions are easily determined by known procedures because "acceptability" arises mostly from emulsion characteristics-rather than from a major change in drug availability.

Dimethicone is a mixture of fully methylated linear siloxane polymers end-blocked with trimethylsiloxy units. These materials are commercially available from several suppliers at varying viscosities ranging from about 0.65 to about centistokes 2,500,000, (Cst), with lower molecular weight polymers exhibiting the lower viscosities up to about a weight of about 30,000 and viscosity of about 1000 Cst, at which polymer chain entanglement occurs, resulting in a leveling in properties.

A preferred dimethicone utilized herein has a viscosity of about 100 to about 300 Cst, and more preferably about 150 to about 250 Cst. [1 Cst=1 cps.]

Cetyl alcohol can be substituted by $C_{12}$–$C_{18}$ alkyl such as lauryl, myristyl, and stearyl alcohols. Methylparaben and propylparaben can be substituted by $C_1$–$C_5$ alkyl paraben, or other suitable preservatives.

Any pharmacologically suitable acid can be used in place of phosphoric acid to adjust the pH of the composition.

Other compounds that can be used in place of squalene include acetylated lanolin. Substitutions for imidurea include DMDM Hydantoin. Emulsifying wax can be replaced with cetylalcohol:steareth-20 whereas stearamidopropyldimethyl amine can be used in place of white wax.

It should also be understood that in addition to the aforementioned carrier ingredients and substitutions, a pharmaceutical formulation described herein can include, as appropriate, one or more additional carrier ingredients such as buffers, binders, surface active agents, additional thickeners and preservatives (including antioxidants), lubricants, and the like. It is also contemplated that a penetration enhancer can be included to permit the active ingredient to penetrate the skin more effectively. One contemplated penetration enhancer is 2-n-nonyl-1,3-dioxolane, knows as SEPA (Soft Enhancer for Percutaneous Absorption). SEPA can be used at about two weight percent (2 wt %) to about twenty weight percent (20 wt %). Fragrances and/or odor masking compounds can also be added.

Process

As noted earlier, a process for preventing and treating a Type I hypersensitivity reaction is contemplated here. Broadly, a compound whose structure corresponds to that of formula I, or a pharmacologically acceptable salt, ester or amide thereof, as active ingredient, dissolved or dispersed in a pharmacologically acceptable carrier is topically administered (applied) to a human patient.

If the purpose of application is prevention of a Type I reaction the composition is applied to those areas of the skin likely to be exposed an allergen. The compound is present in the composition in an amount sufficient to provide a preventively effective amount (a reaction preventing amount) of active ingredient compound over the period of administration. This amount ranges between about 0.02 g and about 0.04 g to about 0.2 g per treatment.

A composition is administered by topically applying the composition to an area likely to be exposed to allergen. The area can then be covered, but is preferably left open to the air. This treatment can be repeated as necessary to maintain an effective amount of the compound on the skin to be protected. Typically application is repeated every 6–8 hours until danger of allergen exposure is removed.

Efficacy of a contemplated process of prevention can be assessed by visual inspection for any reaction sites after known exposure to an allergen.

When the purpose of application is treatment of a Type I reaction site, a compound whose structure corresponds to that of formula I, or a pharmacologically acceptable salt, ester or amide thereof, as active ingredient, dissolved or dispersed in a pharmacologically acceptable carrier is topically administered (applied) to a cutaneous Type I reaction site of a human patient.

The compound is present in the composition in amount sufficient to provide a therapeutically effective amount (a symptom-reducing amount) of active ingredient compound over the period of administration. This amount ranges between about 0.02 g and about 0.4 g per treatment, and more preferably about 0.05 g to about 0.1 g per treatment.

The composition is administered by topically applying the composition to an area affected by the reaction. The site can then be covered, but is again preferably left open to the air. This treatment can be repeated a plurality of times such as several times per day for 7 days, or until the reaction and the symptoms associated with it disappear.

The duration of a particular treatment can vary depending upon the size, type and severity of the reaction. Typical administration lasts about 3 days.

Administration is very easily carried out on an out-patient basis.

Efficacy of a contemplated process for treatment of a reaction site can be assessed by visual inspection of the reaction site and by assessment of the severity of the pruritus perceived by the patient. The inflammation and irritation caused by the reaction typically begins to noticeably decrease after 15–30 minutes. Treatment is then continued as necessary until the reaction has subsided.

Example I

Exemplary Topical Preparation

A topical preparation for prevention and treatment of Type I hypersensitivity reactions in humans was prepared using the ingredients shown below for the preparation of 60 kilograms of a 4 percent cromolyn sodium cream.

| Ingredient | % W/W |
| --- | --- |
| Cromolyn sodium | 4.00 |
| Emulsifying wax, N.F. | 9.00 |
| PPG-2 Myristyl Ether Propionate | 2.50 |
| Polyoxy-10-Oleyl Ether, N.F. | 1.00 |
| Squalene, U.S.P. | 4.00 |
| White Wax, N.F. | 2.00 |
| Dimethicone, N.F. | 1.00 |
| Cetyl Alcohol, N.F. | 3.00 |
| Propylparaben, N.F. | 0.10 |
| Purified Water, U.S.P. | 68.80 |
| Glycerin, U.S.P. | 2.50 |
| Edetate Disodium Dehydrate, U.S.P. | 0.10 |
| Propylene Glycol, U.S.P. | 1.50 |
| Methylparaben, N.F. | 0.20 |
| Imidurea, N.F. | 0.30 |
| Phosphoric Acid, N.F. | q.s |
| pH value | 5.5 |
| viscosity (25° C.) | 60,000 cps0 |

The cream is prepared by the following procedure. Percentage of total weight is given in parenthesis.

Step 1. Charge the main mixing kettle with 25.68 kg of purified water (42.80%) and heat to 75°–80° C. Add 1.50 kg of glycerin (2.50%), 60 g of disodium EDTA U.S.P. (0.10%) and 900 g of propylene glycol (1.50%) individually while mixing at 30 rpm. Add 120 g of methylparaben N.F. (0.20%) and mix for 5 minutes at 30 rpm to disperse. Reduce speed to 20 rpm and mix for ½ hour.

Step 2. In a separate container, heat 5.40 kg of emulsifying wax N.F. (9.00%), 1.50K of PPG-2 myristyl ether propionate (2.50%), 600 g polyoxy-10 oleyl ether N.F. (1.00%), 2.40 kg squalene U.S.P. (4.00%), 1.20 kg white wax (2.00%), 600 g dimethicone N.F. (1.00%), 1.80 kg cetyl alcohol (3.00%) and 60 g propylparaben N.F. (0.10%) to 75°–80° C. Mix at 1700 rpm for 5 minutes.

Step 3. At 75°–80° C., add Step #2 to Step #1 with mixing at 40 rpm. Mix at 40 rpm speed for ½ hour.

Step 4. Cool evenly to 35°–40° C. over a 60 minute period with mixer at 20 rpm.

Step 5. Premix 600 g of purified water U.S.P. (1.00%) and 180 g of imidurea N.F. (0.30%) in a separate container at 250 rpm on the Dayton Gearmixer. Mix manually for 15 minutes. This premix phase should be totally clear before addition to the batch.

Step 6. Add the mixture from step #5 to that at Step #4 and mix well for 10 minutes at 10 rpm.

Step 7. In a separate container premix 15.00 kg of purified water (25.00%) and 2.40 kg of cromolyn sodium U.S.P.

(4.00%) using the lightnin' mixer at 1750 rpm for 20 minutes and check for uniformity.

Step 8. Add the contents of step #7 to the batch and mix for ½ hour at 20 rpm.

Step 9. Adjust pH to 5.5 with phosphoric acid N.F. if necessary.

Two sets of samples from the top, middle and bottom of the kettle are removed and submitted for cromolyn sodium, methylparaben and propylparaben analysis and other physical tests.

The foregoing description is intended as illustrative and is not to be taken as limiting. Still other variations within the spirit and scope of this invention are possible and will readily present themselves to those skilled in the art.

I claim:

1. A pharmaceutical composition comprising a therapeutically effective amount the compound 1,3-bis-(2-carboxychromon-5-yloxy)-2-hydroxypropane, or a pharmacologically acceptable salt, ester or amide thereof as the active ingredient dissolved or dispersed in a pharmacologically acceptable carrier; said pharmacologically acceptable carrier being an oil-in-water emulsion comprising:

(a) a water phase, (b) an oil phase, and (c) emulsifier; said oil phase comprising a wax, squalene, a $C_2$–$C_4$ polypropyleneglycol, a $C_{12}$–$C_{18}$ alkyl ether with 2–4 PPG groups per molecule and silicone oil; and said emulsifier is emulsifying wax and a mixture of a $C_2$–$C_4$ acyl polypropyleneglycol $C_{12}$–$C_{18}$ alkyl ether with 2–4 PPG groups per molecule and a polyoxyethyleneglycol $C_{14}$–$C_{26}$ ether having an average of 8–12 PEG groups per molecule.

2. The composition claim 1 wherein the pH value of said oil-in-water emulsion is between about 3 and about 8.

3. The composition of claim 1 wherein said wax is a mixture of white wax and emulsifying wax.

4. The composition of claim 1 wherein said PPG group is PPG-2-myristyl ether propionate and said PEG group is polyoxyethylene-10-oleyl ether.

5. The composition of claim 1, wherein the pharmacologically acceptable carrier also includes a penetration enhancer to aid in absorption by the skin of said compound.

* * * * *